United States Patent
Singh et al.

(10) Patent No.: US 6,248,802 B1
(45) Date of Patent: *Jun. 19, 2001

(54) ISOCYANATE COMPOSITIONS FOR BLOWN POLYURETHANE FOAMS

(76) Inventors: Sachchida Singh, 7 Rittenhouse Sq., Sicklerville, NJ (US) 08081; Steven Burns, 1101 Belmont Ave., Westmont, NJ (US) 08108

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/096,389

(22) Filed: Jun. 11, 1998

Related U.S. Application Data

(60) Provisional application No. 60/050,952, filed on Jun. 13, 1997, and provisional application No. 60/050,906, filed on Jun. 13, 1997.

(51) Int. Cl.[7] ......................................................... C08J 9/14
(52) U.S. Cl. .......................... 521/131; 521/130; 521/155; 521/170; 521/174; 521/160
(58) Field of Search ..................................... 521/155, 170, 521/174, 130, 131, 160; 252/182.2; 560/26, 359

(56) References Cited

U.S. PATENT DOCUMENTS

| | | |
|---|---|---|
| 5,096,933 | 3/1992 | Volkert . |
| 5,426,127 | 6/1995 | Doerge . |
| 5,436,277 * | 7/1995 | Narayan et al. ...................... 521/160 |
| 5,530,034 * | 6/1996 | Narayan et al. ...................... 521/159 |

FOREIGN PATENT DOCUMENTS

| | | |
|---|---|---|
| 0 308 733 | 3/1989 | (EP) . |
| 0 320 134 | 6/1989 | (EP) . |

* cited by examiner

*Primary Examiner*—John M. Cooney, Jr.
(74) *Attorney, Agent, or Firm*—Kevin J. Boland

(57) ABSTRACT

Rigid polyurethane foams are prepared from an isocyanate composition containing diphenylmethane diisocyanate, three ring oligomers of polyphenylene polymethylene polyisocyanate and higher homologues of polyphenylene polymethylene polyisocyanate.

26 Claims, No Drawings

ISOCYANATE COMPOSITIONS FOR BLOWN POLYURETHANE FOAMS

This application claims the benefit of prior provisional applications 06/050,952 and 60/050,906 both of which were filed on Jun. 13, 1997.

The present invention is directed to processes for the production of rigid polyurethane foams and reaction systems for use therein. More specifically, the present invention is directed to processes for the production of rigid polyurethane foam utilizing a specific polyisocyanate composition, an isocyanate-reactive composition and hydrofluorocarbon or hydrocarbon blowing agents.

Rigid polyurethane foams have many known uses, such as in building materials and thermal insulation. Such foams are known to have superior structural properties, outstanding initial and long term thermal insulation and good fire retardation properties.

Rigid polyurethane foams have conventionally been prepared by reacting appropriate polyisocyanate and isocyanate-reactive compositions in the presence of a suitable blowing agent. With regard to blowing agents, chlorofluorocarbons (CFC's) such as CFC-11 ($CCl_3F$) and CFC-12 ($CCl_2F_2$) have been used most extensively as they have been shown to produce foams having good thermal insulation properties, low flammability and excellent dimensional stability. However, in spite of these advantages, CFC's have fallen into disfavor, as they have been associated with the depletion of ozone in the earth's atmosphere, as well as possible global warming potential. Accordingly, the use of CFC's has been severely restricted.

Hydrochlorofluorocarbons (HCFC's) such as HCFC 141b ($CCl_2FCH_3$) and HCFC22($CHClF_2$) have become a widely used interim solution. However, HCFC's have also been shown to cause a similar depletion of ozone in the earth's atmosphere and accordingly, their use has also come under scrutiny. In fact, the widespread production and use of HCFCs is scheduled to end shortly.

Therefore, there has existed a need to develop processes for the formation of rigid polyurethane foams which utilize blowing agents having a zero ozone depletion potential and which still provide foams having excellent thermal insulation properties and dimensional stability.

A class of materials which have been investigated as such blowing agents include various hydrocarbons such as n-pentane, n-butane and cyclopentane. The use of such materials is well-known and disclosed, e.g., in U.S. Pat. Nos. 5,096,933, 5,444,101, 5,182,309, 5,367,000 and 5,387,618. However, known methods for producing foams with such blowing agents and reaction systems used in such methods have not been found to produce rigid polyurethane foams having commercially attractive physical properties at densities which are sufficiently low to make their use feasible. In short, the properties associated with such hydrocarbon blown foams have generally been inferior to CFC and HCFC blown foams.

Attention has also turned to the use of hydrofluorocarbons (HFC's) including 1,1,1,3,3-pentafluoropropane (HFC 245fa); 1,1,1,3,3-pentafluorobutane (HFC 365mfc); 1,1,1,2-tetrafluoroethane (HFC 134a); and 1,1-difluoroethane (HFC 152a). The use of such materials as blowing agents for rigid polyurethane foams is disclosed, e.g., in U.S. Pat. Nos. 5,496,866; 5,461,084; 4,997,706; 5,430,071; and 5,444,101. However, as with hydrocarbons, attempts to produce rigid foams with such materials have generally not resulted in foams having structural, thermal and thermal properties comparable to those attained using CFC- 11 as the blowing agent.

The majority of attempts to solve this problem have centered around the blending of different hydrofluorocarbons, hydrocarbons or the blending of hydrocarbons with hydrofluorocarbons and/or other blowing agents. Such attempts have met with limited success.

Accordingly, there remains a need for a process for the production of rigid polyurethane foam which utilizes hydrofluorocarbon or hydrocarbon blowing agents and which provides foams having excellent physical properties.

This objective is obtained by the present invention which utilizes polymeric polyisocyanates of a specific composition in the process for the production of rigid polyurethane foam with hydrofluorocarbon or hydrocarbon blowing agents. The present invention provides foams having improved physical and thermal insulation properties.

The present invention is directed to a process for making rigid polyurethane foams comprising reacting:

(1) a polyphenylene polymethylene polyisocyanate composition;

(2) an isocyanate-reactive composition containing a plurality of isocyanate-reactive groups which are useful in the preparation of rigid polyurethane or urethane-modified polyisocyanurate foams;

(3) a hydrofluorocarbon or hydrocarbon blowing agent;

(4) optionally, water or other carbon dioxide evolving compounds, and wherein said polyphenylene polymethylene polyisocyanate comprises (a) a 15 to 42 percent by weight, based on 100% of the polyisocyanate component (1), of diphenylmethane diisocyanate;

(b) 3-ring oligomers of polyphenylene polymethylene polyisocyanate (henceforth referred as triisocyanate) in an amount such that the ratio of diisocyanate to triisocyanate is between about 0.2 to about 1.8; and (c) the remainder being higher homologues of polyphenylene polymethylene polyisocyanate.

The present invention is further directed to reaction system useful for the preparation of rigid polyurethane foams comprising (1) a polyphenylene polymethylene polyisocyanate composition;

(2) an isocyanate-reactive composition containing a plurality of isocyanate-reactive groups which are useful in the preparation of rigid polyurethane or urethane-modified polyisocyanurate foams;

(3) a hydrofluorocarbon or hydrocarbon blowing agent;

(4) optionally, water or other carbon dioxide evolving compounds, and wherein said polyphenylene polymethylene polyisocyanate comprises:

(a) a 15 to 42 percent by weight, based on 100% of the polyisocyanate component (1), of diphenylmethane diisocyanate;

(b) 3-ring oligomers of polyphenylene polymethylene polyisocyanate (henceforth referred as triisocyanate) in an amount such that the ratio of diisocyanate to triisocyanate is between about 0.2 to about 1.8; and (c) the remainder being higher homologues of polyphenylene polymethylene polyisocyanate.

The polyphenylene polymethylene polyisocyanates used in the present invention are those of Formula I

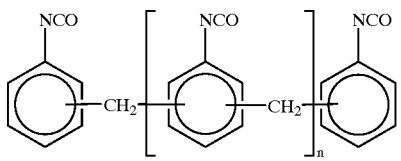

The 3-ring oligomers of component 1 (b) are those represented by Formula I where n=1. The higher homologues of component 1(c) are those represented by Formula I where n>1.

The polyphenylene polymethylene polyisocyanate composition (1) used in the present invention comprises about 15 to about 42 percent, preferably about 20 to about 40 percent and more preferably 24 to about 38 percent by weight, based upon 100 percent of the polyisocyanate component, of diphenylmethane diisocyanates. Diphenylmethane diisocyanate in the form of its 2,2', 2,4' and 4,4' isomers and mixtures thereof may be used as in the present invention. Any variation of the 2,2', 2,4' and 4,4' isomers may be utilized.

The polyphenylene polymethylene polyisocyanate composition (1) further comprises the triisocyanate component in an amount such that the ratio of diisocyanate to triisocyanate is between 0.2 to 1.8 and preferably between about 0.33 to about 1.8. Thus, the actual triisocyanate content is determined based upon the amount of diphenylmethane diisocyanate in the polyphenylene polymethylene composition (1) utilizing the above-stated ratio. The amount is on a percent by weight basis based on 100 percent by weight of the total polyisocyanate composition.

For purposes of clarification, if the amount of diphenylmethane diisocyanate in a given polyphenylene polymethylene polyisocyanate composition is 30 percent and the ratio of diisocyanate to triisocyanate is 1.5, the amount of triisocyanate which must be incorporated into the polyphenylene polymethylene polyisocyanate composition would then be 20 percent by weight based upon 100 percent by weight of the total composition. As used herein, the term "triisocyanate" means all isomers of 3-ring oligomers of polyphenylene polymethylene polyisocyanate (i.e., n=1 in Formula I) containing three phenyl, two methyl and three isocyanate groups. Seven possible isomers of triisocyanate are described in "Chemistry and Technology of Isocyanates" by Henri Ulrich, John Wiley & Sons Inc., p. 388 (1996).

The remainder of the polyphenylene polymethylene polyisocyanate composition comprises higher homologues of polyphenylene polymethylene polyisocyanate. The higher homologues include all of those which are higher than tri, i.e., tetraisocyanate, heptaisocyanate, hexaisocyanate, etc (i.e., n>1 in Structure 1). Suitable higher homologues are described in "The Polyurethanes Book", edited by George Woods, John Wiley & Sons Publisher (1987). The amount of higher homologues contained within the polyphenylene polymethylene polyisocyanate composition is generally about 10 to about 77 and preferably about 19 to about 69 percent, based on 100 percent by weight of the total composition.

The higher homologue component (c) may further comprise higher functionality isocyanates modified with various groups containing ester groups, urea groups, biuret groups, allophanate groups, carbodiimide groups, isocyanurate groups, uretdione groups and urethane groups. Such modified isocyanates and methods for the preparation are known in the art.

The polyphenylene polymethylene polyisocyanate composition (1) is used in an amount of about 35 to about 70 of the total reaction system.

The polyphenylene polymethylene polyisocyanate composition (1) may be prepared by methods known to those skilled in the art. Suitable methods are disclosed, e.g., in "Chemistry and Technology of Isocyanates" Ulrich, John Wiley & Sons Inc. (1996). In general, the polyphenylene polymethylene polyisocyanate compositions are prepared by the reaction of aniline with formaldehyde under acidic conditions to form amines. This is followed by phosgenation and thermal cleavage of the resulting material into a mixture of isocyanate homologues. The amount of diphenylmethane diisocyanate, triisocyanate and higher homologues in the composition can be manipulated by adjusting the aniline to formaldehyde ratio and/or the reaction conditions. For example, a higher aniline to formaldehyde ratio results in a polyphenylene polymethylene polyamine which contains higher amounts of the diphenylmethane diamine component and the triamine component and a correspondingly lower yield of the higher homologue component. Therefore, phosgenation and thermal cleavage of the resulting polyphenylene polymethylene polyamine yields a polyphenylene polymethylene polyisocyanate product which contains higher amounts of the diphenylmethane diisocyanate and the triisocyanate and lower amounts of the higher homologues of isocyanate. Moreover, the composition of the polyphenylene polymethylene polyisocyanate component which contains can also be controlled by partial fractionation to separate diphenylmethane diisocyanate along with a variety of isocyanate modified reaction routes.

The isocyanate-reactive compositions (2) useful in the present invention include any of those known to those skilled in the art to be useful for the preparation of rigid polyurethane foams. Examples of suitable isocyanate-reactive compositions having a plurality of isocyanate-reactive groups include polyether polyols, polyester polyols and mixtures thereof having average hydroxyl numbers of from about 20 to about 1000 and preferably about 50 to 700 KOH/g and hydroxyl functionalities of about 2 to about 8 and preferably about 2 to about 6. Other isocyanate-reactive materials which can be used in the present invention include hydrogen terminated polythioethers, polyamides, polyester amides, polycarbonates, polyacetals, polyolefins, polysiloxanes, and polymer polyols.

Suitable polyether polyols include reaction products of alkylene oxides, e.g., ethylene oxide and/or propylene oxide, with initiators containing from 2 to 8 active hydrogen atoms per molecule. Suitable initiators include polyols, e.g., diethylene glycol, glycerol, trimethylolpropane, triethanolamine, pentaerythritol, sorbitol, methyl glucoside, mannitol and sucrose; polyamines, e.g., ethylene diamine, toluene diamine, diaminodiphenylmethane and polymethylene polyphenylene polyamines; amino alcohols, e.g., ethanolamine and diethanolamine; and mixtures thereof. Preferred initiators include polyols and polyamines.

Suitable polyester polyols include those prepared by reacting a carboxylic acid and/or a derivative thereof or a polycarboxylic anhydride with a polyhydric alcohol. The polycarboxylic acids may be any of the known aliphatic, cycloaliphatic, aromatic, and/or heterocyclic polycarboxylic acids and may be substituted, (e.g., with halogen atoms) and/or unsaturated. Examples of suitable polycarboxylic acids and anhydrides include oxalic acid, malonic acid, glutaric acid, pimelic acid, succinic acid, adipic acid, suberic acid, azelaic acid, sebacic acid, phthalic acid, isophthalic acid, terephthalic acid, trimellitic acid, trimellitic acid anhydride, pyromellitic dianhydride, phthalic acid anhydride, tetrahydrophthalic acid anhydride, hexahydrophthalic acid anhydride, endomethylene tetrahydrophthalic acid anhydride, glutaric acid anhydride acid, maleic acid, maleic acid anhydride, fumaric acid, and dimeric and trimeric fatty acids, such as those of oleic acid which may be in admixture with monomeric fatty acids. Simple esters of polycarboxylic acids may also be used such as terephthalic acid dimethylester, terephthalic acid bisglycol and extracts thereof. While the aromatic polyester polyols can be prepared from substantially pure reactant materials as listed above, more complex ingredients may be advantageously used, such as the side-streams, waste or scrap residues from the manufacture of phthalic acid, phthalic anhydride, terephthalic acid, dimethyl terephthalate, polyethylene terephthalate, and the like.

The polyhydric alcohols suitable for the preparation of polyester polyols may be aliphatic, cycloaliphatic, aromatic, and/or heterocyclic. The polyhydric alcohols optionally may include substituents which are inert in the reaction, for example, chlorine and bromine substituents, and/or may be unsaturated. Suitable amino alcohols, such as monoethanolamine, diethanolamine or the like may also be used. Examples of suitable polyhydric alcohols include ethylene glycol, propylene glycol, polyoxyalkylene glycols (such as diethylene glycol, polyethylene glycol, dipropylene glycol and polypropylene glycol), glycerol and trimethylolpropane.

The isocyanate-reactive material is used in an amount of about 20% to about 70% and preferably about 30% to about 60% of the total reaction system.

The present process further comprises reacting polyphenylene polymethylene polyisocyanate composition (1) and isocyanate-reactive composition (2) with one or more hydrofluorocarbon or hydrocarbon blowing agents which are vaporizable under foam forming conditions. The hydrofluorocarbon blowing agents useful in the present invention include: 1,1,1,3,3-pentafluoropropane (HFC-245fa); 1,1,1,3,3-pentafluorobutane (HFC 365mfc); 1,1,1,4,4,4-heptafluorobutane (HFC 356mff); 1,1-difluoroethane (HFC 152a), 1,1,1,2-tetrafluoroethane (HFC 134a) and mixtures thereof. Preferred hydrofluorocarbons include 1,1,1,3,3-pentafluoropropane; 1,1,1,3,3-pentafluorobutane and 1,1,1,2-tetrafluoroethane. Suitable hydrocarbons include butane, isobutane, isopentane, n-pentane, cyclopentane, I-pentene, n-hexane, iso-hexane, 1-hexane, n-heptane, isoheptane, and mixtures thereof. Preferably the hydrocarbon blowing agent is isopentane, n-pentane, cyclopentane and mixtures thereof. The most preferred hydrocarbon blowing agent for use in the present invention is a blend of isopentane to n-pentane in a ratio of 80:20 to 99:1 parts by weight.

The hydrofluorocarbon blowing agent should be used in an amount of about 2% to about 20% and preferably about 4 to about 15 percent of the entire reaction system.

The hydrocarbon blowing agent should be used in an amount of about 2% to about 20% and preferably about 4% to about 15% of the entire reaction system.

Other physical blowing agents may also be used in the present process in combination with the hydrocarbon blowing agents. Suitable blowing agents include 1,1,1,3,3-pentafluoropropane (HFC-245fa), 1,1,1,2-tetrafluorethane (HFC- 134a), 1,1 -difluoroethane (HFC- 152a), difluoromethane (HFC-32), chlorodifluoromethane (HCFC-22), and 2-chloropropane. When used, these blowing agents may be mixed into the isocyanate-reactive component, the isocyanate component and/or as a separate stream to the reaction system.

Vaporizable non-hydrofluorocarbons, such as 2-chloropropane, isopentane, cyclopentane may also be used in the present process in combination with the hydrofluorocarbon blowing agents. When used, the blowing agents may be mixed into the isocyanate-reactive component, the isocyanate component and/or as a separate stream to the reaction system.

The present process may optionally further comprise reacting the polyphenylene polymethylene polyisocyanate, the isocyanate-reactive composition and the hydrofluorocarbon or hydrocarbon blowing agents in the presence of water in an amount of 0.1% to about 5% and preferably about 0.2% to about 4% of the total reaction system. Water reacts to generate carbon dioxide to act as an additional blowing agent. Other carbon dioxide evolving compounds may further be used in place of or in addition to water. Such compounds include carboxylic acids and cyclic amines.

The reaction system may further comprise one or more auxiliary agents or additives as needed for one or more particular purposes. Suitable auxiliaries and additives include crosslinking agents, such as triethanolamine and glycerol; foam stabilizing agents or surfactants, such as siloxane-oxyalkylene copolymers and oxyethylene-oxyalkylene copolymers; catalysts, such as tertiary amines, (e.g., dimethylcyclohexylamine, pentamethyldiethylenetriamine, 2,4,6-tris(dimethylaminomethyl) phenol, and triethylenediamine), organometallic compounds (e.g., potassium octoate, potassium acetate, dibutyl tin dilaurate), quaternary ammonium salts (e.g., 2-hydroxypropyl trimethylammonium formate) and N-substituted triazines (N,N', N"-dimethylaminopropylhexahydrotriazine); flame retardants such as organo-phosphorous compounds ( such as organic phosphates, phosphites, phosphonate, polyphosphates, polyphosphites, polyphosphonate, ammonium polyphosphate (for example triethyl phosphate, diethyl ethyl phosphonate, tris(2-chloropropyl)-phosphate) and halogenated compounds (such as tetrabromophthalate esters, chlorinated parrafins); viscosity reducers such as propylene carbonate and 1-methyl-2-pyrrolidinone; infrared opacifiers such as carbon black, titanium dioxide and metal flakes; cell-size reducing compounds, such as inert, insoluble fluorinated compounds and perfluorinated compounds; reinforcing agents, such as glass fibers and ground up foam waste; mold release agents, such as zinc stearate; antioxidants, such as butylated hydroxy toluene; and pigments such as azo-/diazo dyestuff and phthalocyanines. The amount of such auxiliary materials or additives is generally between about 0.1 to about 20%, preferably between about 0.3 to about 15% and most preferably between about 0.5 to about 10%, by weight based on 100% of the total foam formulation.

In operating the process for making rigid foams according to this invention, the known one-shot, prepolymer or semi-prepolymer techniques may be used together with conventional mixing methods, such as impingement mixing. The rigid foam may be produced in the form of slabstock, mouldings, cavity filling, sprayed foam, frothed foam or laminates with other material such as paper, metal, plastics, or wood-board. See, e.g., Saunders and Frisch, *Polyurethanes Chemistry and Technology, Part II,* Interscience Publishers, New York (1962), and the references cited for various methods of polyurethane formation.

The present invention further encompasses rigid polyurethane foams produced by the processes disclosed above.

The present invention will now be illustrated by reference to the following specific, non-limiting examples.

EXAMPLES

Unless otherwise noted, in the Examples set forth below, all temperatures are expressed in degrees Celsius and amounts of all formulation components are expressed in parts by weight.

The following materials are used and referred to in the examples.

Stepanpol® PS-2352 is an aromatic polyester polyol available from Stepan Co. which comprises a phthalic anhydride/glycol-based (polyol having a hydroxyl value of 240 KOH/g and a viscosity of 3,000 cPs at 25° C.

TCPP is tri(beta-chloropropyl) phosphate available from Great Lakes Chemical Corporation.

Pelron(® 9540A is potassium octoate in diethylene glycol available from Pelron Corp.

Polycat® 8 is dimethyl cyclohexylamine available from Air Products Corp.

Tegostab® B8466 is a silicone surfactant available from Goldschmidt Corporation.

Borger Isopentane is an isopentane product containing 97.5% isopentane and 2.5% n-pentane available from Phillips Petroleum Company.

Hydrofluorocarbon HFC245fa (pressurized) available from AlliedSignal.

Polyisocyanate A contained 32% of diphenyl methane diisocyanates, had a ratio of diisocyanate to triisocyanate of 1.2 (providing the triisocyanate in an amount of 26.7%); and 41.3% of higher homologues. Isocyanate B had a diphenyl methane diisocyanate content of 44%; a diisocyanate to triisocyanate ratio of 1.8 (providing 24.4% of triphenyldimethane triisocyanate); and 31.6% of higher homologues. Both Isocyanate A and B had an NCO content of 31%.

EXAMPLE 1

A polyol blend was prepared by mixing 100 parts of Stepanpol PS2352 with 14 parts of TCPP, 3 parts of Pelron 9540A. 0.6 parts of Polycat 8, 2.65 parts of Tegostab B8466 and 1.3 parts of water in a high speed mixer at room temperature.

Rigid foams were prepared from the formulations set forth in Table 1 below. The polyol blend was added to the 'B side' tank of an Edge-Sweets high pressure impingement mix dispense machine. An appropriate amount of isopentane, based on the compositions set forth in Table 1, was then added to the 'B side' and mixed vigorously using an air-mixer attached to the tank. The isocyanate was then added to the 'A side' tank attached to the dispense machine.

The machine parameters were set as follows:

| | |
|---|---|
| A side temperature (° F.) | 70 |
| B side temperature (° F.) | 70 |
| Mix pressure (psig) | 2,000 |
| A side pump rpm | 70 |
| B side pump rpm | adjusted to give appropriate isocyanate weight ratio as in Table 1 |
| Dispense rate (g/sec) | 180 |

The foaming ingredients were shot from the dispense machine into #10 Lily cup and reactivity was measured on free use foam.

The structural properties were measured on core specimens taken from 7"×7"×15" foams made by dispensing foam ingredients into an appropriate cardboard box.

Foam core density was measured according to ASTM D1622. The high temperature dimensional stability was measured following ATM D2126. The compressive strength was measured parallel and perpendicular to foam rise direction according to ASTM D1621 Procedure A. The thermal properties of the foams were measured according to ASTM C518 on core foam taken from 2"×14"×14" blocks. Fire performance was tested according to ASTM D3014 to measure Butler Chimney weight retention.

TABLE 1

| | Foam #1 | Foam #2 | Foam #3 | Foam #4 |
|---|---|---|---|---|
| 'B-side' | | | | |
| Polyol Blend | 34.8 | 34.8 | 34.5 | 34.5 |
| Isopentane | 6.2 | 6.2 | 6.6 | 6.6 |
| 'A-side' | | | | |
| Isocyanate A | 59 | — | 58.9 | — |
| Isocyanate B | — | 59 | — | 58.9 |
| Isopentane Reactivities: | | | | |
| Cream Time, seconds | 4 | 5 | 6 | 5 |
| Gel Time, seconds | 24 | 24 | 24 | 26 |
| Tack-Free Time, seconds | 42 | 43 | 62 | 51 |
| Foam Properties: | | | | |
| Core Density, pcf | 1.9 | 1.9 | 1.75 | 1.75 |
| Structural Properties: Dimensional stability, % linear change | | | | |
| 7 days at −25° C. | −1 | −2.9 | −1.9 | −3.6 |
| 7 days at 93° C./amb | 2 | 2.6 | 2.7 | 3.4 |
| 7 days at 70° C./97% RH | 2.2 | 3.4 | 3.5 | 3.6 |
| Compressive Strength, psi | | | | |
| Parallel to rise | 39.4 | 34.3 | 37.6 | 33.3 |
| Perpendicular to rise | 12.3 | 8.8 | 11.3 | 11.1 |
| Thermal Properties: k-factor in BTU. in/ft$^2$. hr. ° F. | | | | |
| Initial | 0.15 | 0.15 | 0.15 | 0.15 |
| After 8 wks at 140° F. | 0.17 | 0.18 | 0.18 | 0.18 |
| Fire Properties: | | | | |
| Butler Chimney, % wt. retained | 93 | 88 | 88 | 86 |

It can be clearly seen from the data set forth in Table 1, that Foam 1 prepared with Isocyanate A according to the present invention provides a rigid polyurethane foam which is superior in structural, thermal and fire performance properties in comparison to Foam 2. Foam 2 was prepared with Isocyanate B which is outside the scope of the present invention.

Foams 3 and 4 were prepared at densities typical of CFC blown foam. As set forth in Table 1, Foam 3 prepared with Isocyanate A, according to the present invention, has superior structural thermal and fire performance properties in comparison to Foam 4. Foam 4 was prepared with Isocyanate B which is outside the scope of the present invention.

Moreover, Foam 3 (according to the present invention) can be compared to Foam 2. The dimensional stability and Butler chimney weight retention are nearly identical for the two foams. Also, the compression strength, along with the initial and aged K factors of Foam 3 are superior to those for Foam 2. Accordingly, the data demonstrates that foams prepared with a polyisocyanate composition according to the present invention (Isocyanate A) have better performance properties at lower densities that those of foam prepared with conventional isocyanates at higher densities.

EXAMPLE 2

A polyol blend was prepared by mixing 100 parts of Stepanpol PS2352 with 4.5 parts of Pelron 9540A. 1.0 parts of Polycat 8, 2.0 parts of Tegostab B8466 and 0.3 parts of water in a high speed mixer at room temperature.

Rigid foams were prepared from the formulations set forth in Table 2 below. The polyol blend was added to the 'B side' tank of an Edge-Sweets high pressure impingement mix dispense machine. An appropriate amount of HFC245fa, based on the compositions set forth in Table 2, was then added to the 'B side' and mixed vigorously using an air-mixer attached to the tank. The isocyanate was then added to the 'A side' tank attached to the dispense machine.

The machine parameters were set as follows:

| | |
|---|---|
| A side temperature (° F.) | 70 |
| B side temperature (° F.) | 70 |
| Mix pressure (psig) | 2,000 |
| A side pump rpm | 70 |
| B side pump rpm | adjusted to give appropriate isocyanate weight ratio as in Table 2 |
| Dispense rate (g/sec) | 200 |

The foaming ingredients were shot from the dispense machine into #10 Lily cup and reactivity was measured on this free rise foam.

The structural properties were measured on core specimens taken from 7"×7"×15" foams made by dispensing foam ingredients into an appropriate cardboard box.

Foam core density was measured according to ASTM D1622. The high temperature dimensional stability was measured following ATM D2126. The compressive strength was measured parallel and perpendicular to foam rise direction according to ASTM D1621 Procedure A. The thermal properties of the foams were measured according to ASTM DC518 on core foam taken from 2"×14"×14" blocks. Fire performance was tested according to ASTM D3014 to measure Butler Chimney weight retention.

TABLE 2

| | Foam #5 | Foam #6 | Foam #7 | Foam #8 |
|---|---|---|---|---|
| 'B-side' | | | | |
| Polyol Blend | 34.4 | 34.4 | 34.0 | 34.0 |
| HFC245fa | 13.7 | 13.7 | 14.6 | 14.6 |
| 'A-side' | | | | |
| Isocyanate A | 51.9 | — | 58.4 | — |
| Isocyanate B | — | 51.9 | — | 58.4 |
| Reactivities: | | | | |
| Cream Time, seconds | 3 | 3 | 3 | 3 |
| Gel Time, seconds | 11 | 11 | 11 | 11 |
| Tack-Free Time, seconds | 15 | 14 | 13 | 13 |
| Foam Properties: | | | | |
| Core Density, pcf | 2.14 | 2.14 | 2.02 | 2.02 |
| Structural Properties: | | | | |
| Dimensional stability, % linear change | | | | |
| 7 days at −25° C. | −1.1 | −3.6 | −1.3 | −5.2 |
| 7 days at 93° C./amb | 2.3 | 4.4 | 3.6 | 5 |
| Compressive Strength, psi | | | | |
| Parallel to rise | 47.9 | 34 | 40.2 | 32 |
| Perpendicular to rise | 21.3 | 11.5 | 13.9 | 10.8 |
| Thermal Properties: | | | | |

TABLE 2-continued

| | Foam #5 | Foam #6 | Foam #7 | Foam #8 |
|---|---|---|---|---|
| k-factor in BTU. in/ft². hr. ° F. | | | | |
| Initial | 0.128 | 0.132 | 0.129 | 0.130 |

It can be clearly seen from the data set forth in Table 2, that Foam 5, prepared with Isocyanate A according to the present invention, provides a rigid polyurethane foam which is superior in structural, thermal and fire performance properties in comparison to Foam 6. Foam 6 was prepared with Isocyanate B which is outside the scope of the present invention.

Foams 7 and 8 were prepared at densities typical of CFC blown foam. As set forth in Table 2, Foam 7, prepared with Isocyanate A according to the present invention, has superior structural thermal and fire performance properties in comparison to Foam 8. Foam 8 was prepared with Isocyanate B which is outside the scope of the present invention.

Moreover, Foam 7 (according to the present invention) can be compared to Foam 6. The dimensional stability value is nearly identical for the two foams. Also, the compressive strength, along with the initial and aged K factors of Foam 7 are superior to those for Foam 6. Accordingly, the data demonstrates that foams prepared with a polyisocyanate composition according to the present invention have better performance properties at lower densities that those of foam prepared with conventional isocyanates at higher densities.

What is claimed is:

1. A reaction system for preparation of rigid polyurethane foam comprising:
   (1) a polyphenylene polymethylene polyisocyanate composition including,
      (a) 15 to 42 percent by weight, based on 100% of the polyisocyanate composition, of diphenylmethane diisocyanate,
      (b) 3-ring oligomers of polyphenylene polymethylene polyisocyanate in an amount such that the ratio of (a) to (b) is equal to from about 0.2 to about 1.8, and
      (c) higher homologues of polyphenylene polymethylene polyisocyanate;
   (2) an isocyanate-reactive composition containing a plurality of isocyanate-reactive groups; and
   (3) a blowing agent selected from hydrofluorocarbon and hydrocarbon, and mixtures thereof.

2. The reaction system of claim 1, wherein the amount of the diphenylmethane diisocyanate is equal to from about 20 to about 40 percent.

3. The reaction system of claim 1, wherein the amount of the diphenylmethane diisocyanate is equal to from about 24 to about 38 percent.

4. The reaction system of claim 1, additionally including water or other carbon dioxide evolving compounds.

5. The reaction system of claim 1, wherein the blowing agent is hydrofluorocarbon.

6. The reaction system of claim 5, wherein the hydrofluorocarbon is present in an amount equal to from about 2 to about 20 percent by weight, based on the weight of the reaction system.

7. The reaction system of claim 5, wherein the hydrofluorocarbon is present in an amount equal to from about 4 to about 15 percent by weight, based on the weight of the reaction system.

8. The reaction system of claim 5, wherein the hydrofluorocarbon is selected from the group consisting of 1,1,1,3,3-pentafluoropropane (HFC-245fa), 1,1,1,3,3-pentafluorobutane (HFC 365mfc), 1,1,1,4,4,4-heptafluorobutane (HFC 356mff), 1,1-difluoroethane (HFC 152a), 1,1,1,2-tetrafluoroethane (HFC 134a), and mixtures thereof.

9. The reaction system of claim 5, wherein the blowing agent is hydrocarbon.

10. The reaction system of claim 9, wherein the hydrocarbon is present in an amount equal to from about 2 to about 20 percent by weight, based on the weight of the reaction system.

11. The reaction system of claim 9, wherein the hydrocarbon is present in an amount equal to from about 4 to about 15 percent by weight, based on the weight of the reaction system.

12. The reaction system of claim 9, wherein the hydrocarbon is selected from the group consisting of butane, isobutane, isopentane, n-pentane, cyclopentane, 1-pentane, n-hextane, iso-hexane, 1-hexane, n-heptane, isoheptane, and mixtures thereof.

13. A reaction system for preparation of rigid polyurethane foam comprising:
  (1) a polyphenylene polymethylene polyisocyanate composition including,
    (a) 15 to 42 percent by weight, based on 100% of the polyisocyanate composition, of diphenylmethane diisocyanate,
    (b) 3-ring oligomers of polyphenylene polymethylene polyisocyanate in an amount such that the ratio of (a) to (b) is equal to from about 0.2 to about 1.8, and
    (c) higher homologues of polyphenylene polymethylene polyisocyanate;
  (2) an isocyanate-reactive composition containing a plurality of isocyanate-reactive groups; and
  (3) an isopentane and n-pentane blend blowing agent.

14. The reaction system of claim 13, wherein the isopentane and n-pentane are present in an isopentane to n-pentane ratio of 80:20 to 99:1 parts by weight.

15. A method for making rigid polyurethane foam comprising reacting:
  (1) a polyphenylene polymethylene polyisocyanate composition including,
    (a) 15 to 42 percent by weight, based on 100% of the polyisocyanate composition, of diphenylmethane diisocyanate,
    (b) 3-ring oligomers of polyphenylene polymethylene polyisocyanate in an amount such that the ratio of (a) to (b) is equal to from about 0.2 to about 1.8, and
    (c) higher homologues of polyphenylene polymethylene polyisocyanate;
  (2) an isocyanate-reactive composition containing a plurality of isocyanate-reactive groups; and
  (3) a blowing agent selected from hydrofluorocarbon and hydrocarbon, and mixtures thereof.

16. The method of claim 15, wherein the amount of diphenylmethane diisocyanate is equal to from about 20 to about 40 percent.

17. The method of claim 15, wherein the amount of diphenylmethane diisocyanate is equal to from about 24 to about 38 percent.

18. The method of claim 15, additionally including water or other carbon dioxide evolving compounds.

19. The method of claim 15, wherein the blowing agent is hydrofluorocarbon.

20. The method of claim 19, wherein the hydrofluorocarbon is present in an amount equal to from about 2 to about 20 percent by weight, based on the weight of the reaction system.

21. The method of claim 19, wherein the hydrofluorocarbon is present in an amount equal to from about 4 to about 15 percent by weight, based on the weight of the reaction system.

22. The method of claim 19, wherein the hydrofluorocarbon is selected from the group consisting of 1,1,1,3,3-pentafluoropropane (HFC-245fa), 1,1,1,3,3-pentafluorobutane (HFC 365mfc), 1,1,1,4,4,4-heptafluorobutane (HFC 356mff), 1,1-difluoroethane (HFC 152a), 1,1,1,2-tetrafluoroethane (HFC 134a), and mixtures thereof.

23. The method of claim 15, wherein the blowing agent is hydrocarbon.

24. The method of claim 23, wherein the hydrocarbon is present in an amount equal to from about 2 to about 20 percent by weight, based on the weight of the reaction system.

25. The method of claim 23, wherein the hydrocarbon is present in an amount equal to from about 4 to about 15 percent by weight, based on the weight of the reaction system.

26. The method of claim 23, wherein the hydrocarbon is selected from the group consisting of butane, isobutane, isopentane, n-pentane, cyclopentane, 1-pentane, n-hextane, iso-hexane, 1-hexane, n-heptane, isoheptane, and mixtures thereof.

* * * * *